United States Patent
Gliner et al.

(10) Patent No.: US 10,271,906 B2
(45) Date of Patent: Apr. 30, 2019

(54) UPDATING A VOLUMETRIC MAP

(71) Applicant: Biosense Webster (Israel) Ltd., Yokneam (IL)

(72) Inventors: Vadim Gliner, Haifa (IL); Assaf Govari, Haifa (IL); Andres Claudio Altmann, Haifa (IL)

(73) Assignee: BIOSENSE WEBSTER (ISRAEL) LTD., Yokneam (IL)

(*) Notice: Subject to any disclaimer, the term of this patent is extended or adjusted under 35 U.S.C. 154(b) by 523 days.

(21) Appl. No.: 14/934,268

(22) Filed: Nov. 6, 2015

(65) Prior Publication Data

US 2017/0128138 A1    May 11, 2017

(51) Int. Cl.
| | |
|---|---|
| A61B 17/24 | (2006.01) |
| A61B 17/00 | (2006.01) |
| A61B 5/06 | (2006.01) |
| A61B 90/00 | (2016.01) |
| A61B 34/20 | (2016.01) |

(52) U.S. Cl.
CPC .............. *A61B 34/20* (2016.02); *A61B 5/062* (2013.01); *A61B 17/24* (2013.01); *A61B 90/00* (2016.02); *A61B 2017/00022* (2013.01); *A61B 2017/00053* (2013.01); *A61B 2034/2051* (2016.02)

(58) Field of Classification Search
CPC .......................... A61B 2034/2051; A61B 34/20
See application file for complete search history.

(56) References Cited

U.S. PATENT DOCUMENTS

| | | |
|---|---|---|
| 8,652,148 B2 | 2/2014 | Zuhars |
| 2003/0208296 A1 | 11/2003 | Brisson et al. |
| 2005/0137599 A1 | 6/2005 | Masini |
| 2008/0281335 A1 | 11/2008 | Fell |
| 2009/0093823 A1* | 4/2009 | Chang ............... A61B 17/24 606/110 |
| 2011/0152684 A1 | 6/2011 | Altmann et al. |
| 2013/0035696 A1 | 2/2013 | Qutub |
| 2013/0060278 A1* | 3/2013 | Bozung ........... A61B 17/32002 606/205 |
| 2014/0093452 A1 | 4/2014 | Ahrens et al. |
| 2015/0018698 A1 | 1/2015 | Safran et al. |

(Continued)

FOREIGN PATENT DOCUMENTS

WO    2014059241 A1    4/2014

OTHER PUBLICATIONS

Ivica Benko: "CARTO 3D mapping lijevog atrija" youtube, Nov. 29, 2014 (Nov. 29, 2014), p. 1 pp., XP054977451, Retrieved from the Internet: URL:https://www.youtube.com/watch?v=GJ5CIGGMqZU.

(Continued)

*Primary Examiner* — Tse W Chen
*Assistant Examiner* — Jason M Ip
(74) *Attorney, Agent, or Firm* — Notaro, Michalos & Zaccaria P.C.

(57) ABSTRACT

A method for guiding a procedure is provided. A volumetric map of an interior portion of a body of a subject is presented, and, during the procedure, in response to movements of a sensor with respect to the portion, the presented volumetric map is updated, by changing a manner in which the presented volumetric map shows areas of the portion from which material was removed by the procedure. Other embodiments are also described.

16 Claims, 2 Drawing Sheets

(56) References Cited

U.S. PATENT DOCUMENTS

2016/0310042 A1* 10/2016 Kesten .................. A61B 17/24

OTHER PUBLICATIONS

Jmandrola: "Fast Anatomical Map: Carto 3", youtube, May 6, 2010 (May 6, 2010), p. 1 pp., / XP054977452, Retrieved from the Internet: URL:https://www.youtube.com/watch?v=kvMADcJDsA8&t=4s.
Extended European Search Report for corresponding application serial No. EP 16197344.1, dated Jul. 6, 2017.

* cited by examiner

UPDATING A VOLUMETRIC MAP

FIELD OF THE INVENTION

Embodiments of the present invention relate to medical procedures, such as otolaryngological shaving procedures, in which tissue or other material is removed from the interior of a subject's body.

BACKGROUND

In some otolaryngological shaving procedures, a physician removes tissue, such as a nasal polyp, from a subject. In some cases, the physician navigates the shaving tool by referring to a volumetric map of the subject's anatomy that was acquired prior to the procedure. Such a volumetric map may be acquired, for example, using computed tomography (CT) or magnetic resonance imaging (MRI).

International Patent Application WO/2014/059241, whose disclosure is incorporated herein by reference, describes a method for fusing information related to structural features and characteristics of a biological sample. The resulting fused image may be imported into a surgical navigation technology intra-operatively to aid in surgical interventions by co-registering the fused image with the patient's anatomical features.

US 2014/0093452, whose disclosure is incorporated herein by reference, provides, in part, fluorocarbon imaging reagents and methods for image-guided treatment and/or diagnosis of a subject with a condition associated with an inflammatory response in an internal organ. The disclosure additionally provides methods for image-guided treatment of myocardial infarction (MI) in a subject.

US 2015/0018698, whose disclosure is incorporated herein by reference, describes a parametric model representing a portion of a heart, constructed using a statistical prior of the shape from a dataset of other instances of the portion. Using a mapping electrode, electrical data is acquired in a plurality of locations in the portion of the heart of a subject. The parametric model is fitted to the electrical data and the statistical prior to produce an isosurface of the portion of the heart and a reconstruction of its shape.

US 2011/0152684, whose disclosure is incorporated herein by reference, describes a method for three-dimensional (3D) mapping that includes acquiring a plurality of two-dimensional (2D) ultrasonic images of a cavity in a body of a living subject, the 2D images having different, respective positions in a 3D reference frame. In each of the 2D ultrasonic images, pixels corresponding to locations within an interior of the cavity are identified. The identified pixels from the plurality of the 2D images are registered in the 3D reference frame so as to define a volume corresponding to the interior of the cavity. An outer surface of the volume is reconstructed, representing an interior surface of the cavity.

SUMMARY OF THE INVENTION

There is provided, in accordance with some embodiments of the present invention, a method for guiding a procedure. A volumetric map of an interior portion of a body of a subject is presented. During the procedure, in response to movements of a sensor with respect to the portion, the presented volumetric map is updated, by changing a manner in which the presented volumetric map shows areas of the portion from which material was removed by the procedure.

In some embodiments, the sensor is coupled to a tool that is used to remove the material.

In some embodiments, updating the presented volumetric map includes updating the presented volumetric map to show as empty the areas from which the material was removed.

In some embodiments, updating the presented volumetric map includes updating the presented volumetric map by coloring the areas from which the material was removed.

In some embodiments, the interior portion of the body of the subject includes a body cavity.

In some embodiments, updating the presented volumetric map includes updating the presented volumetric map to indicate that a portion of tissue that at least partially encloses the body cavity was removed.

In some embodiments, the movements of the sensor include movements of the sensor along tissue that at least partially encloses the body cavity.

In some embodiments, the body cavity includes a nasal cavity of the subject.

In some embodiments, the body cavity includes a sinus cavity of the subject.

In some embodiments, the movements of the sensor include movements of the sensor within the portion.

In some embodiments, the movements of the sensor include movements of the sensor outside of the portion.

In some embodiments, updating the presented volumetric map includes:

automatically computing a surface that defines an extent of movement within the portion that is related to the movements of the sensor, and updating the presented volumetric map, using the surface.

In some embodiments, the extent of movement is an extent of movement of the sensor.

In some embodiments, the extent of movement is an extent of movement of a portion of a tool that is used to remove the material, and automatically computing the surface includes automatically computing the surface based on a relationship between (i) a position and an orientation of the sensor, and (ii) a position of the portion of the tool.

In some embodiments, the sensor includes an electromagnetic sensor.

In some embodiments, the volumetric map includes a computed-tomography-based map of the portion of the body of the subject.

In some embodiments, the volumetric map includes a magnetic-resonance-imaging-based map of the portion of the body of the subject.

In some embodiments, the volumetric map was acquired prior to the procedure using a particular imaging modality, and updating the presented volumetric map includes updating the presented volumetric map without using the particular imaging modality.

There is further provided, in accordance with some embodiments of the present invention, apparatus for guiding a procedure. The apparatus includes a display and a processor. The processor is configured to (i) present, on the display, a volumetric map of an interior portion of a body of a subject, and (ii) during the procedure, in response to movements of a sensor with respect to the portion, update the presented volumetric map, by changing a manner in which the presented volumetric map shows areas of the portion from which material was removed by the procedure.

The present invention will be more fully understood from the following detailed description of embodiments thereof, taken together with the drawings, in which:

DETAILED DESCRIPTION OF EMBODIMENTS

Overview

In some procedures, a physician removes tissue or other material from the interior of a subject's body, e.g., from a body cavity of the subject, using a tool that is inserted into the subject. In some cases, the physician navigates the tool by referring to a volumetric map of the subject's anatomy, such as a CT volume, that was acquired prior to the procedure. As the physician removes the tissue or other material, however, the volumetric map is rendered inaccurate; in particular, the volumetric map continues to show the newly-empty areas as being occupied. Hence, as the procedure progresses, it becomes more and more difficult for the physician to properly navigate the tool. Moreover, the physician is unable to confirm that the tissue or other material was properly removed.

One solution for the latter problem is to perform a post-procedural imaging of the subject. For example, a post-procedural CT volume may be acquired, and this CT volume may then be compared to the initial CT volume, in order to confirm that the procedure was successful. A drawback to this solution, however, is that the physician is not informed in real-time, as the procedure progresses, whether the tissue or other material is being properly removed. Furthermore, acquiring a second CT volume (or MRI volume) of the subject may be time-consuming and/or expensive.

Embodiments of the present invention therefore provide an alternate, superior solution. During the procedure, a sensor is moved within the portion of the subject's body from which material is being removed. The extent of the movements of the sensor provide information as to which areas are empty, and the volumetric map is then updated, as necessary, in response to this information. The process of moving the sensor, and updating the volumetric map in response thereto, is generally fast and inexpensive, and in addition, provides real-time guidance to the physician.

System Description

Figure 1:
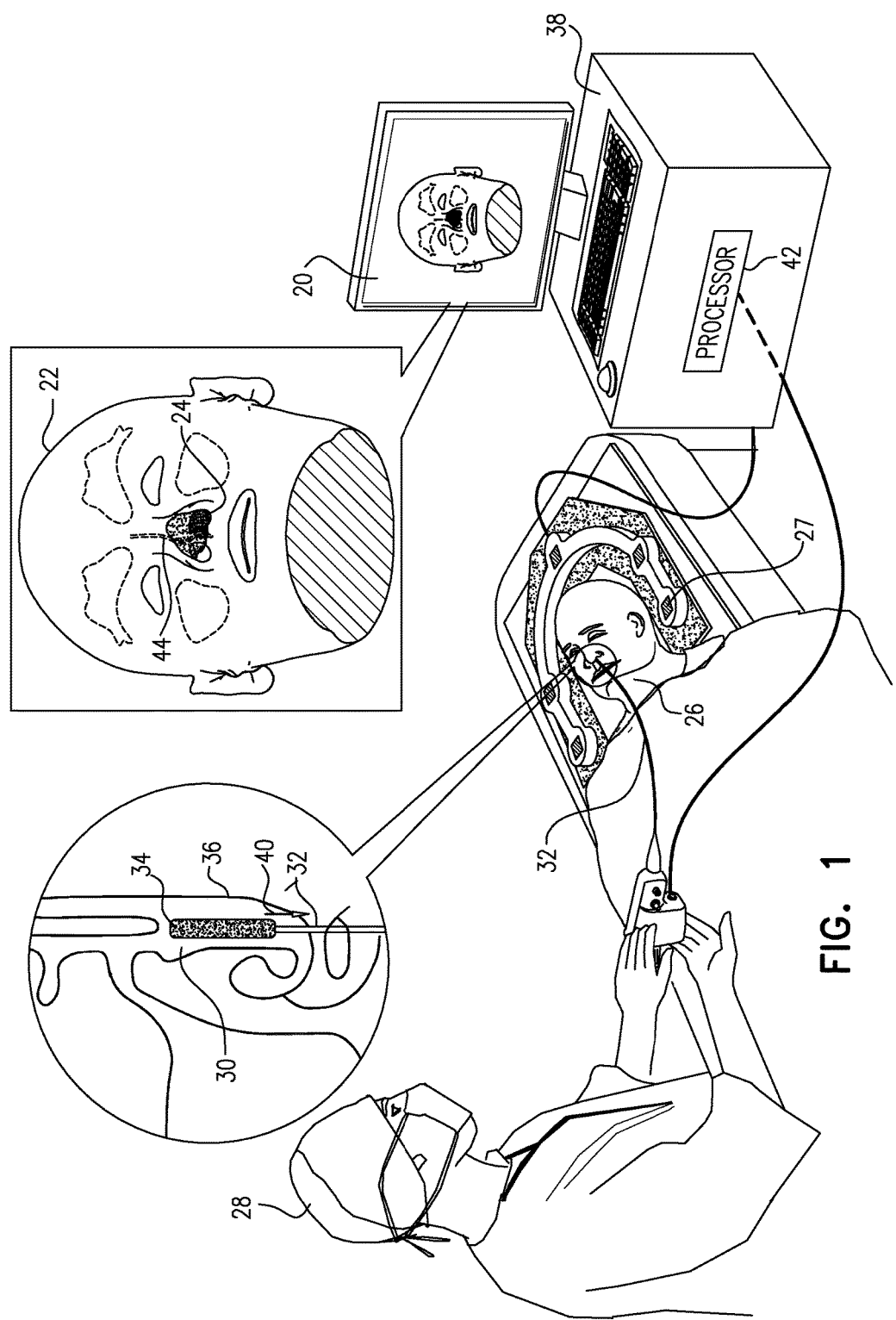
FIG. 1 is a schematic illustration of a system for guiding a procedure, in accordance with some embodiments of the present invention.

Reference is initially made to FIG. 1, which is a schematic illustration of a system for guiding a procedure, in accordance with some embodiments of the present invention. FIG. 1 depicts the performance of an otolaryngological shaving procedure, in which tissue is removed from a body cavity of a subject 26, such as the subject's nasal cavity 30 or sinus cavity. However, it is noted that embodiments described herein are applicable to any relevant procedure during which any kind of material (e.g., tissue, hardened mucus, or a foreign body) is removed from an interior portion of the body of a subject.

Figure 2:
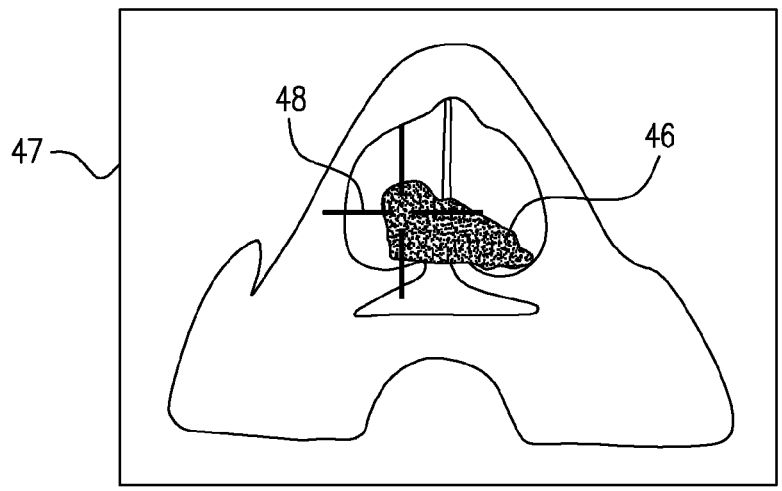
FIG. 2 is a schematic illustration of a two-dimensional slice of a volumetric map, presented in accordance with some embodiments of the present invention.

FIG. 1 shows the operating physician 28 referring to a display 20, such as a computer monitor, on which is presented a volumetric map 22 of the subject's face. Volumetric map 22 may include, for example, a CT-based or MRI-based map, acquired, using the relevant modality, prior to the procedure. As further described below, during the procedure, in real-time, the volumetric map is updated to reflect any changes to the anatomy caused by the procedure. (The images shown on the display in FIGS. 1-2 are derived from a simulation that was performed by one of the inventors.)

Physician 28 is shown holding a guidewire 32, which has been inserted into the subject's nose, such that the distal end of guidewire 32 is positioned within nasal cavity 30. At the distal end of the guidewire is a sensor 34, typically comprising an electromagnetic sensor, such as a coil. The physician moves sensor 34 within the nasal cavity, including, typically, along the tissue 36 that partially encloses the nasal cavity. While the sensor is moved, the sensor receives signals transmitted from external coils 27, which are positioned around the patient's head. In response to receiving the signals from the external coils, the sensor generates a signal 40 that indicates the position and orientation of the sensor. Signal 40 is received by a processor 42, which, for example, may be located within a console 38. In response to the signal, the processor updates the volumetric map, as further described below.

Typically, a technique such as Fast Anatomical Mapping (FAM), described, for example, in US 2011/0152684 to Altmann et al., whose disclosure is incorporated herein by reference, is practiced. The FAM technique automatically computes a surface 24 that defines the extent of the movements of the sensor. In other words, surface 24 bounds a volume within which, but not outside of which, the sensor was moved. As shown in FIG. 1, surface 24 may be presented to the physician as an overlay on the volumetric map. By observing surface 24, the physician is able to see the changes that have occurred to the subject's anatomy as a result of the procedure. For example, in the scenario depicted in FIG. 1, the physician is able to see that a portion of the subject's septum 44 was removed. The physician may then instruct the processor to update the volumetric map, as further described below, to incorporate the changes that were made to the anatomy. Alternatively, the processor may automatically update the volumetric map using surface 24, even without any specific input from the physician.

Typically, a pre-procedural registration is performed between external coils 27 and the volumetric map, such that the location of the sensor—and hence, the location of surface 24—may be expressed in terms of the coordinate system of the volumetric map.

In some embodiments, as depicted in FIG. 1, sensor 34 is disposed separately from the tool that is used to remove the tissue or other material from the subject. In such embodiments, the physician typically alternates between (i) the tool, and (ii) the guidewire, probe, or other instrument that comprises the sensor. For example, the physician may first use an otolaryngological shaver to remove some tissue (e.g., part of the subject's septum) from the subject's nasal cavity. Subsequently, the physician may withdraw the shaver from the subject's nose, insert the sensor, move the sensor within the nasal cavity, and update the volumetric map in response to the movements of the sensor. Subsequently, the physician may withdraw the sensor, reinsert the shaver, and continue to remove tissue as appropriate, using the updated volumetric map for guidance.

In other embodiments, sensor 34 is coupled to, e.g., by being fixedly or reversibly integrated with, the tool that is used for the procedure (e.g., an otolaryngological shaver). The coupling of the sensor to the tool obviates the need to alternate between instruments, and further provide enhanced navigation of the tool, in that the position of the tool may be derived, in real-time, from the measured position of the sensor. In some embodiments, the sensor is disposed at the distal end of the tool. In other embodiments, the sensor is disposed at a more proximal location, e.g., in the tool handle. In such latter embodiments, the sensor need not necessarily be moved within the portion of the subject's body on which the procedure is performed. Rather, the sensor may be moved outside of the portion (e.g., entirely outside of the subject's body), and the volumetric map may be updated based on (i) the movements of the sensor, and (ii) the known, fixed relationship between the position and orientation of the sensor and the position of the distal end of the tool. For example, the known, fixed relationship may be used to compute the extent of movement of the distal end of the tool, based on the measured movements of the sensor. In response thereto, surface 24 may be constructed, and subsequently used to update the volumetric map.

In light of the above, it may be stated generally that:

(i) The volumetric map may be updated in response to any movements of the sensor with respect to the relevant portion of the subject's body. Such movements may include movements within the portion (as depicted in FIG. 1), movements outside of the portion, or a combination of both.

(ii) Surface 24 may define the extent of any movement within the relevant portion of the subject's body that is related to the movements of the sensor. In other words, surface 24 may define the extent of movement of the sensor itself, or alternatively, for embodiments in which the sensor is moved outside of the portion of the subject's body, movement of the distal end of, or any other relevant portion of, a shaving tool, guidewire, or any other instrument to which the sensor is coupled.

Reference is now additionally made to FIG. 2, which is a schematic illustration of a two-dimensional slice 47 through the volumetric map shown in FIG. 1, presented in accordance with some embodiments of the present invention. A slice such as slice 47 may be presented to the physician on display 20, alternatively or additionally to the three-dimensional map of FIG. 1, to help guide the procedure. (The cross-hairs 48 indicate to the physician the current position of the sensor.)

As noted above, processor 42 updates the volumetric map in response to movements of the sensor. In updating the volumetric map, the processor changes the manner in which the volumetric map shows the areas from which tissue or other material was removed. Typically, surface 24, which, as described above, is computed in response to the movements of the sensor, is used to update the volumetric map. For example, in slice 47, the area that previously contained the removed portion of the septum is colored, in that a colored patch 46 is displayed in that area (and in surrounding areas). Patch 46 may be derived by projecting the volume bounded by surface 24 onto slice 47, and coloring the projection. Alternatively, patch 46 may be derived directly from the movements of the sensor, i.e., patch 46 may be derived by coloring every location that is visited by the sensor.

Alternatively to showing a colored patch, the volumetric map may be updated to simply show the newly-empty areas as empty. For example, the voxels bounded by surface 24 may be set to black, thus indicating that these voxels are empty. The blacked-out portions of the volumetric map would then be displayed in the three-dimensional view of FIG. 1, and/or the two-dimensional view of FIG. 2.

FIGS. 1 and 2 collectively illustrate a scenario in which the volumetric map is updated to indicate the removal of a portion of tissue that at least partially encloses a body cavity. Alternatively, the volumetric map may be updated to indicate the removal of any type of tissue or material, including, for example, a nasal polyp.

Figure 3:
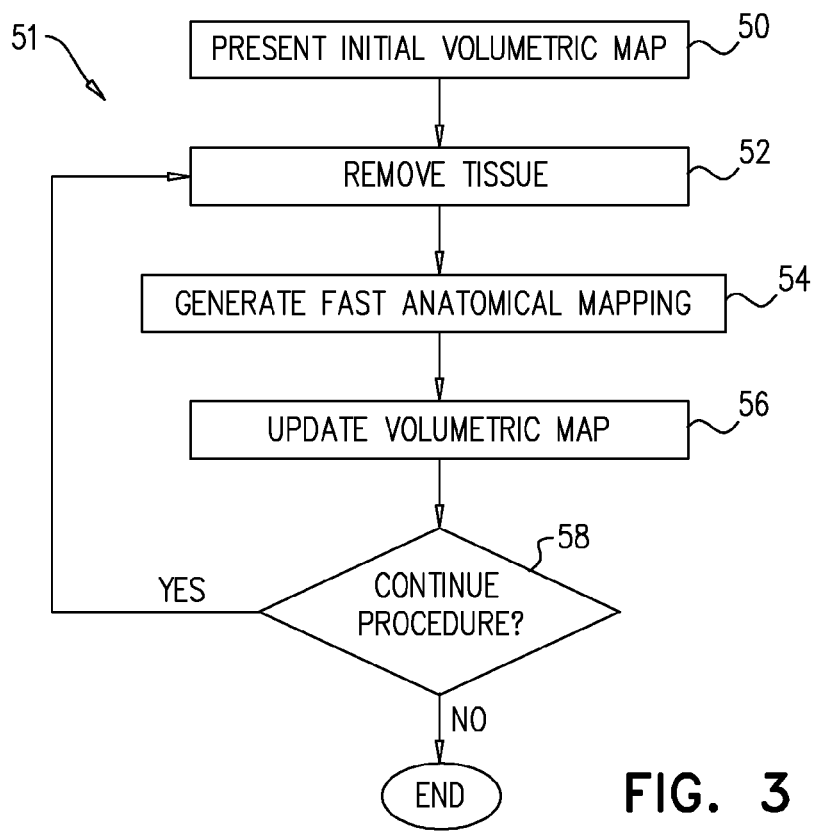
FIG. 3 is a flow diagram for a method for guiding a procedure, in accordance with some embodiments of the present invention.

Reference is now made to FIG. 3, which is a flow diagram for a method 51 for guiding a procedure, in accordance with some embodiments of the present invention. Method 51 begins with a presenting step 50, at which the initial volumetric map is presented to the physician. As noted above, the volumetric map may include a CT or MRI volume, acquired prior to the procedure.

Using the volumetric map for guidance, at a tissue-removal step 52, the physician removes tissue from the subject. Subsequently, at a FAM-generating step 54, the physician uses the sensor, as described above, to generate a Fast Anatomical Mapping (FAM) of the relevant portion of the subject's anatomy. Subsequently, at an updating step 56, the volumetric map is updated in light of the FAM, as described above. The physician then consults the updated volumetric map, and decides, at a decision step 58, whether to continue the procedure. If the physician decides not to continue, the procedure ends. Otherwise, method 51 returns to tissue-removal step 52, at which the physician removes more tissue from the subject, using the updated volumetric map for guidance.

In general, processor 42 may be embodied as a single processor, or a cooperatively networked or clustered set of processors. Processor 42 is typically a programmed digital computing device comprising a central processing unit (CPU), random access memory (RAM), non-volatile secondary storage, such as a hard drive or CD ROM drive, network interfaces, and/or peripheral devices. Program code, including software programs, and/or data are loaded into the RAM for execution and processing by the CPU and results are generated for display, output, transmittal, or storage, as is known in the art. The program code and/or data may be downloaded to the computer in electronic form, over a network, for example, or it may, alternatively or additionally, be provided and/or stored on non-transitory tangible media, such as magnetic, optical, or electronic memory. Such program code and/or data, when provided to the processor, produce a machine or special-purpose computer, configured to perform the tasks described herein.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method for guiding a nasal cavity procedure, the procedure comprising removal of a portion of a septum of a patient the method for guiding comprising the steps of:
presenting a combination view, the combination view comprising a volumetric map of an interior portion of a body of a subject in combination with a two-dimensional slice through the volumetric map, the two-dimensional slice comprising cross-hairs which indicate a position of a sensor; and during the procedure, in response to movements of the sensor with respect to the portion, updating the presented volumetric map, by changing a manner in which the presented volumetric map shows areas of the portion from which material was removed by the procedure, wherein updating the presented volumetric map comprises:

automatically computing a surface that defines an extent of movement within the portion that is related to the movements of the sensor, wherein the surface is used to update the volumetric map, wherein, in the two-dimensional slice, an area which previously contained a removed portion of a septum is displayed as a colored patch, wherein the colored patch is derived by projecting a volume bounded by the surface onto the slice and coloring the projected volume, and updating the presented volumetric map, using the surface, and wherein the presented volumetric map was acquired using a particular imaging modality, and the step of updating the presented volumetric map comprises updating the presented volumetric map without using the particular imaging modality.

2. The method according to claim 1, wherein the sensor is coupled to a tool that is used to remove the material.

3. The method according to claim 1, wherein the interior portion of the body of the subject includes a body cavity.

4. The method according to claim 3, wherein updating the presented volumetric map comprises updating the presented volumetric map to indicate that a portion of tissue that at least partially encloses the body cavity was removed.

5. The method according to claim 3, wherein the movements of the sensor include movements of the sensor along tissue that at least partially encloses the body cavity.

6. The method according to claim 3, wherein the body cavity includes a nasal cavity of the subject.

7. The method according to claim 3, wherein the body cavity includes a sinus cavity of the subject.

8. The method according to claim 1, wherein the movements of the sensor include movements of the sensor within the portion.

9. The method according to claim 1, wherein the movements of the sensor include movements of the sensor outside of the portion.

10. The method according to claim 1, wherein the extent of movement is an extent of movement of the sensor.

11. The method according to claim 1, wherein the sensor includes an electromagnetic sensor.

12. The method according to claim 1, wherein the volumetric map includes a computed-tomography-based map of the portion of the body of the subject.

13. The method according to claim 1, wherein the volumetric map includes a magnetic-resonance-imaging-based map of the portion of the body of the subject.

14. The method according to claim 1, wherein the volumetric map was acquired prior to the procedure using a particular imaging modality, and wherein updating the presented volumetric map comprises updating the presented volumetric map without using the particular imaging modality.

15. Apparatus for guiding a sinus cavity procedure, the apparatus comprising:

a display; and a processor, configured to:

present, on the display, a combination view, the combination view comprising a volumetric map of an interior portion of a body of a subject in combination with a two-dimensional slice through the volumetric map, the two-dimensional slice comprising cross-hairs which indicate a position of a sensor, and during the procedure, in response to movements of a sensor with respect to the portion, update the presented volumetric map, by changing a manner in which the presented volumetric map shows areas of the portion from which material was removed by the procedure, wherein updating the presented volumetric map comprises:

automatically computing a surface that defines an extent of movement within the portion that is related to the movements of the sensor, wherein the surface is used to update the volumetric map, wherein, in the two-dimensional slice, an area which previously contained a removed portion of the septum is displayed as a colored patch, wherein the colored patch is derived by projecting a volume bounded by the surface onto the slice and coloring the projected volume, and updating the presented volumetric map, using the surface, and wherein the presented volumetric map was acquired using a particular imaging modality, and the step of updating the presented volumetric map comprises updating the presented volumetric map without using the particular imaging modality.

16. The apparatus according to claim 15, wherein the extent of movement is an extent of movement of the sensor.

* * * * *